United States Patent
Hollander

(10) Patent No.: US 9,220,630 B2
(45) Date of Patent: Dec. 29, 2015

(54) IMPLANTABLE VALVE ASSEMBLY FOR MALE CONTRACEPTION

(76) Inventor: Mitchell B. Hollander, Bloomfield Hills, MI (US)

( * ) Notice: Subject to any disclaimer, the term of this patent is extended or adjusted under 35 U.S.C. 154(b) by 605 days.

(21) Appl. No.: 13/587,484

(22) Filed: Aug. 16, 2012

(65) Prior Publication Data
US 2014/0048076 A1   Feb. 20, 2014

(51) Int. Cl.
| | | |
|---|---|---|
| *A61F 6/06* | (2006.01) | |
| *A61F 5/48* | (2006.01) | |
| *F17D 1/16* | (2006.01) | |
| *F17D 1/18* | (2006.01) | |
| *B08B 3/00* | (2006.01) | |
| *B08B 5/00* | (2006.01) | |
| *F16K 5/00* | (2006.01) | |
| *G05D 13/10* | (2006.01) | |
| *F16K 13/00* | (2006.01) | |
| *A61F 6/24* | (2006.01) | |
| *F16K 11/02* | (2006.01) | |
| *F16K 11/00* | (2006.01) | |
| *A61F 6/20* | (2006.01) | |
| *A61F 6/22* | (2006.01) | |
| *A61F 6/00* | (2006.01) | |
| *A61F 6/02* | (2006.01) | |
| *F16K 11/044* | (2006.01) | |
| *F16K 11/052* | (2006.01) | |

(52) U.S. Cl.
CPC ... *A61F 6/24* (2013.01); *A61F 6/00* (2013.01); *A61F 6/02* (2013.01); *A61F 6/20* (2013.01); *A61F 6/22* (2013.01); *F16K 11/00* (2013.01); *F16K 11/02* (2013.01); *F16K 11/044* (2013.01); *F16K 11/052* (2013.01)

(58) Field of Classification Search
CPC ............ Y10T 137/00; Y10T 137/0318; Y10T 137/0491; Y10T 137/0508; F16K 11/00; F16K 11/02; F16K 11/044; F16K 11/052; F16K 11/0525; A61F 6/00; A61F 6/02; A61F 6/20; A61F 6/22; A61F 6/24
USPC ........... 128/830, 831, 833, 839, 84, 843, 842, 128/885; 137/14, 15.06, 15.22, 56, 247.13, 137/247.19, 247.21, 249–250; 251/89.5, 251/205–208, 904
See application file for complete search history.

(56) References Cited

U.S. PATENT DOCUMENTS

| | | | | |
|---|---|---|---|---|
| 3,731,670 | A * | 5/1973 | Loe | 600/30 |
| 3,777,737 | A * | 12/1973 | Bucalo | 128/843 |
| 3,812,841 | A * | 5/1974 | Isaacson | 600/29 |
| 4,143,853 | A * | 3/1979 | Abramson | 251/149.1 |
| 8,616,212 | B1 * | 12/2013 | Logan | 128/831 |
| 8,647,310 | B2 * | 2/2014 | Fangrow et al. | 604/236 |
| 2011/0067705 | A1 * | 3/2011 | Kennedy | 128/843 |

* cited by examiner

*Primary Examiner* — Alireza Nia
*Assistant Examiner* — Brandon L Jackson
(74) *Attorney, Agent, or Firm* — Dickinson Wright PLLC

(57) ABSTRACT

A valve assembly adapted for implantation into the vas deferens of a male patient. The valve assembly is operable in a first mode to block the flow of sperm and in a second mode to permit the flow of sperm. The surgeon is permitted to shift the valve assembly between its first and second functional modes by moving a moveable valve member. The valve assembly includes a valve retention feature for releasably retaining the valve member is a selected position associated with each of the two distinct functional modes.

11 Claims, 4 Drawing Sheets

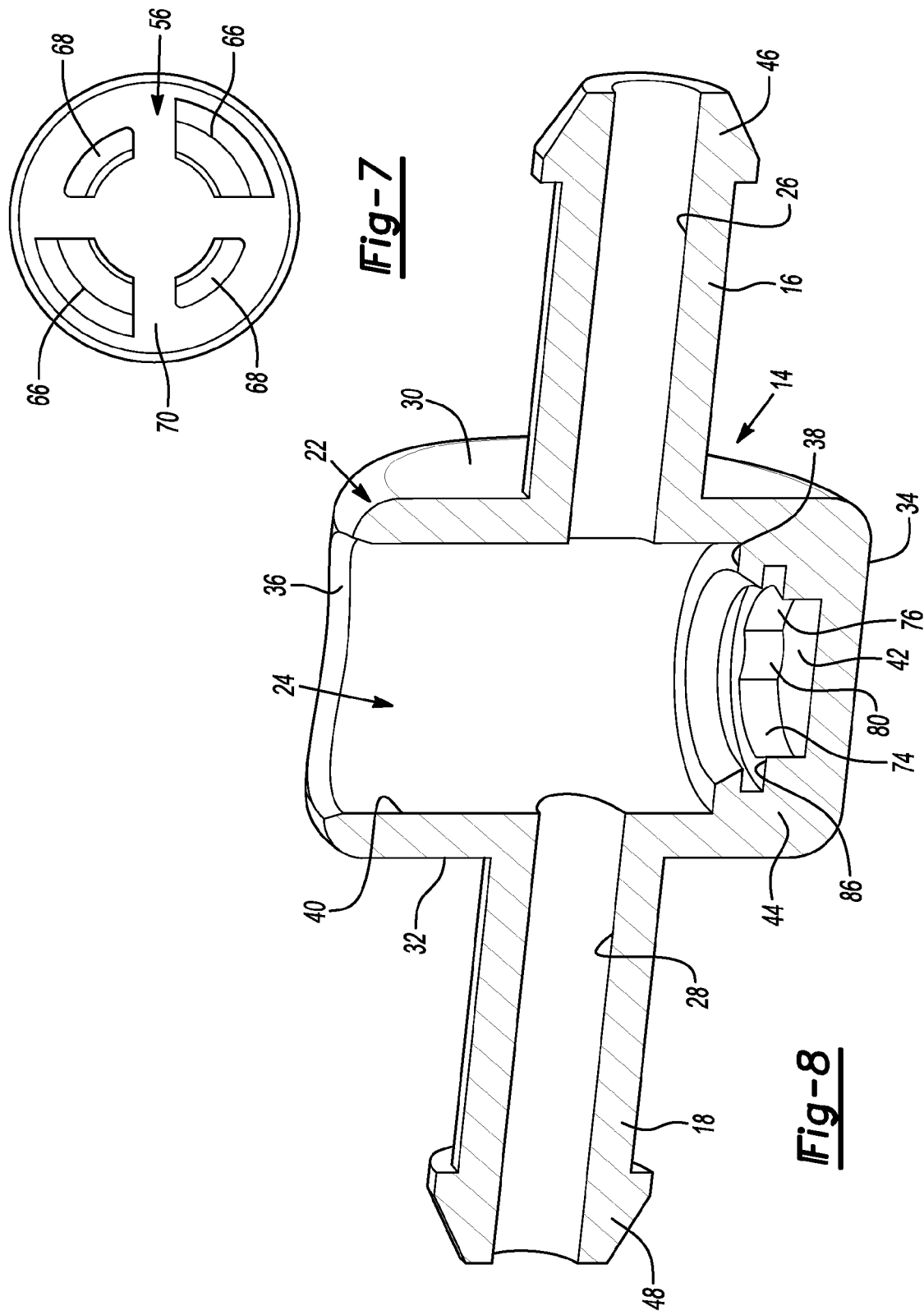

IMPLANTABLE VALVE ASSEMBLY FOR MALE CONTRACEPTION

FIELD

The present disclosure relates generally to implantable male contraception devices and, more specifically, relates to an implantable dual-mode valve assembly and a method of implanting such a valve assembly in the vas deferens.

BACKGROUND

This section provides background information related to the present disclosure which is not necessarily prior art.

Male contraception is most commonly achieved by a surgical vasectomy. Conventionally, a surgical vasectomy may be performed by the traditional method of removing the vas deferens completely or by cutting and sealing the vas deferens, commonly referred to as a "keyhole" or non-scalpel vasectomy. Patients undergoing either type of vasectomy should consider the procedure to be permanent and non-reversible. In some limited cases, the vasectomy may be reversed by a second surgical procedure known as a vasovasostomy. While vasovasostomy can be an effective means for treating pain arising from vasectomy complications, the procedure provides no guarantee that the patient's reproductive capabilities will be completely restored. Furthermore, as with most microsurgical procedures, the vasovasostomy can be extremely costly. Accordingly, male patients desiring an effective contraception method often hesitate when considering a vasectomy due to the potential physical side-effects and the essentially irreversible effects of the surgery.

Recently, methods of definitive male contraception utilizing an intra vas implant have been developed as an alternative to traditional vasectomy surgery. The intra vas implant is implanted into the vas deferens, blocking the path of sperm from the testicles to the urethra, to achieve male contraception. Two common types of implantable devices include injectable implants and sutured implants. The injectable implants utilize an injectable liquid polymer which is injected into the vas deferens and subsequently hardens to create a plug. The injectable polymer contraception method may be reversible by surgically removing the plugs. The sutured implants utilize a silicone plug that is implanted into each vas deferens and anchored to the wall by microsutures. Similar to the injectable plugs, the silicone plugs can be surgically removed.

Thus, a need exists to develop a permanent implant that provides male contraception and yet can be reversed without the need for secondary surgical procedures.

SUMMARY

This section provides a general summary of the disclosure, and is not intended to be a comprehensive disclosure of its full scope or all of its features, advantages and uses.

It is an object of the present disclosure to provide an implantable valve assembly for male contraception and a method of implanting such a contraceptive valve assembly.

It is yet another object of the present disclosure to provide an intra vas valve assembly that may easily be implanted into the vas deferens of a male patient.

It is a further object of the present disclosure to provide a dual-mode valve assembly operable in a first mode to block the flow of sperm through the vas deferens and in a second mode to permit such flow of sperm through the vas deferens, thereby establishing a permanently implanted device for selectable male contraception.

In accordance with these and other objects, a male contraception vas implant is disclosed and hereinafter referred to as an implantable valve assembly. The valve assembly can include a housing and a valve member. The housing can include a central body section defining a valve chamber, a tubular inlet section having an inlet passage communicating with the valve chamber, and a tubular outlet section having an outlet passage communicating with the valve chamber. The inlet section and the outlet section of the housing can have ramped end portions for assisting in inserting and retaining the inlet and outlet sections into the free ends of a surgically cut vas deferens. The valve member is installed within the valve chamber of the body section and can include a flow aperture, a tool receipt feature and a valve retention feature. The valve member is operable in a first position to orient the flow aperture so as to prevent fluid communication between the inlet passage and the outlet passage. The valve member is also operable in a second position to orient the flow aperture so as to permit fluid communication between the inlet and outlet passages. The tool receipt feature is provided to permit the surgeon to selectively move the valve member between its first and second positions while the valve retention feature is provided to maintain the valve member in the position selected by the surgeon.

In accordance with one preferred, but non-limiting construction, the implantable valve assembly of the present disclosure can include a cylindrical valve chamber formed in the body section of the housing and a cylindrical valve member disposed within the cylindrical valve chamber. The cylindrical valve member can be rotated by the surgeon between its first and second position using a tool to engage the tool receipt feature that is associated with a first end of the valve member. The valve retention feature is associated with a second end of the valve member and can include a pair of resilient first legs extending into and retained within a retention chamber that is formed in the body section of the housing. The retention chamber has a wall surface configured to resiliently inwardly deflect the first legs upon rotary movement of the valve member between its first and second positions. Upon the valve member being definitively positioned in one of its first and second positions, the configuration of the wall surface in the retention chamber permits the resilient first legs to snapback for retaining the rotary valve member in the selected position. The retention feature can further include a pair of resilient second legs associated with the second end of the valve member and which have radial flange portions resiliently biased into an annular groove formed in the body section of the housing. The radial flange portions are disposed within the annular groove such that the second legs function to inhibit removal of the valve member from the valve chamber of the housing.

In accordance with another preferred, but non-limiting construction, the implantable valve assembly of the present disclosure can include a slot-shaped valve chamber formed in the body section of the housing and a disc-shaped valve member disposed in the valve chamber. The valve member can be translated between its first and second positions via a tool engaging a tool receipt feature associated with at least one end of the valve member. The valve retention feature can include a pair of laterally-spaced resilient legs each having a lug formed at its distal end. The lugs can be retained in a pair of complimentary first edge notches formed in the body section to definitively locate the valve member in its first position. Likewise, the lugs can be retained in a pair of complimentary second edge notches formed in the body section to definitively locate the valve member in its second position. In either position, the lugs function to retain the valve member in its desired position and prevent removal of the valve member from the housing.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations thereof such that the drawings are not intended to limit the scope of the present disclosure.

Corresponding reference numerals indicate corresponding elements/parts throughout the several views of the drawings wherein:

FIG. 7 is an end view of the valve member showing components of the retention feature in greater detail;

FIG. 8 is a sectional view of the housing associated with the implantable valve assembly shown in FIGS. 2 through 4;

DETAILED DESCRIPTION

Example embodiments will now be described more fully with reference to the accompanying drawings.

The present disclosure relates generally to an implantable valve assembly that is well-suited for use as a male contraception device when surgically implanted in the vas deferens of a patient. As will be detailed, the valve assembly is intended to be permanently (i.e., non-removeably) implanted and yet function to permit selection between a first or "contraceptive" mode and a second or "reproductive" mode. Accordingly, the valve assembly of the present disclosure can be intentionally switched between functional modes so as to overcome the shortcomings associated with traditional contraceptive surgeries (i.e., vasectomy and vasovasostomy) and prior art removeable plug-type contraceptive implants.

Figure 1:
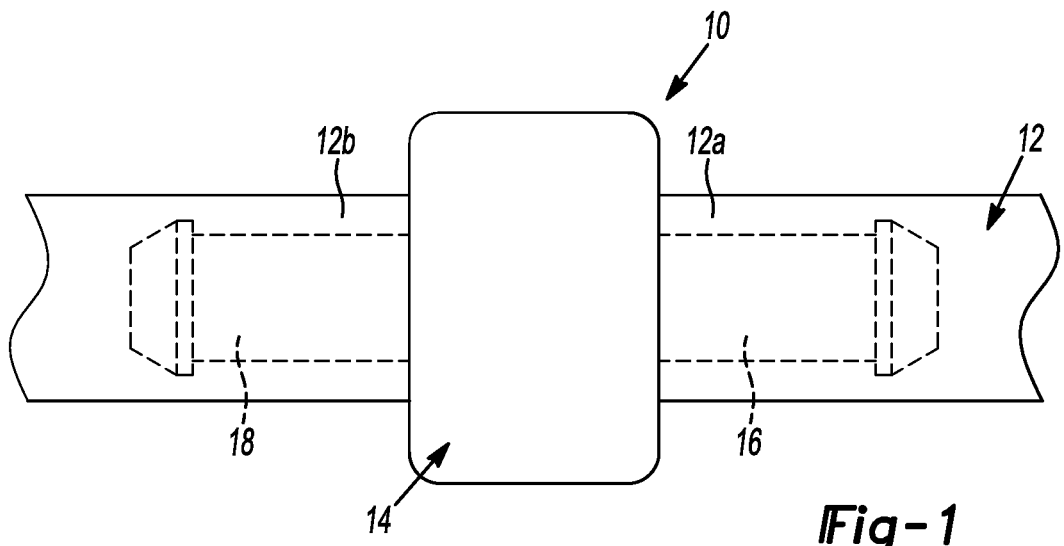
FIG. 1 is a schematic of a valve assembly for male contraception implanted in the vas deferens of a male patient in accordance with the teachings of the present disclosure.
Figure 2:
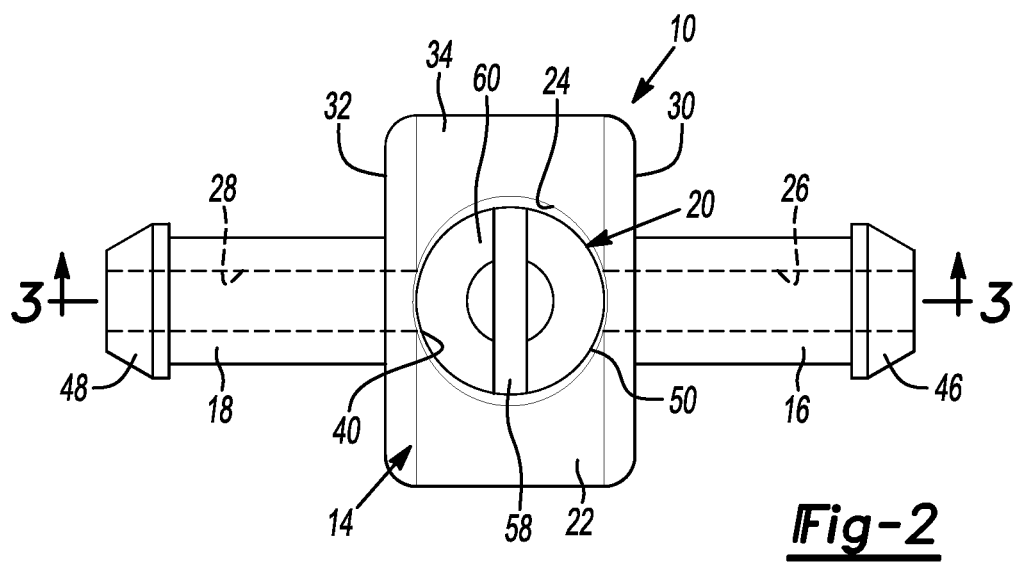
FIG. 2 is a side view of a first exemplary embodiment of the valve assembly shown in FIG. 1 and which is constructed in accordance with the present teachings.
Figure 3:
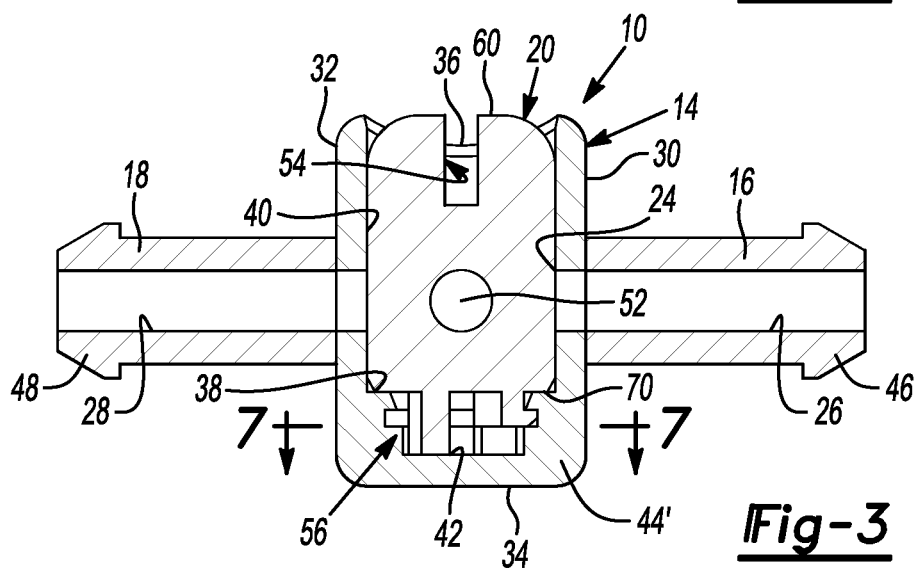
FIG. 3 is a sectional view of the valve assembly taken generally along line A-A of FIG. 2.
Figure 4:
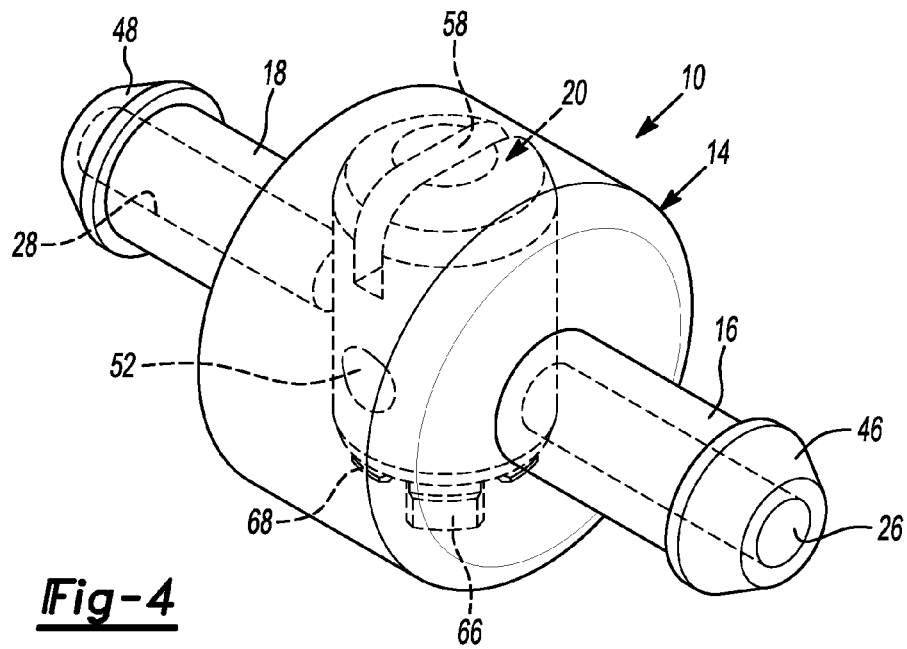
FIG. 4 is a perspective view of the valve assembly shown in FIGS. 2 and 3 with its housing shown in phantom.
Figures 5A, 5B, 6:
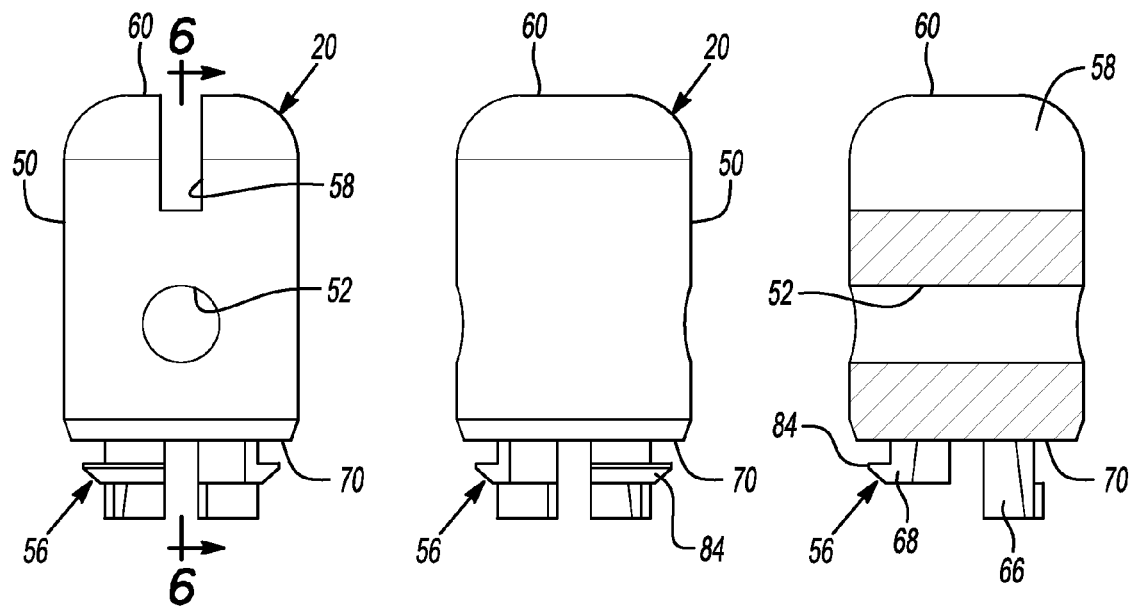
FIGS. 5A and 5B are side views of the valve member associated with the implantable valve assembly shown in FIGS. 2 through 4.
FIG. 6 is a sectional view of the valve member taken generally along line B-B of FIG. 5A.
Figure 9:
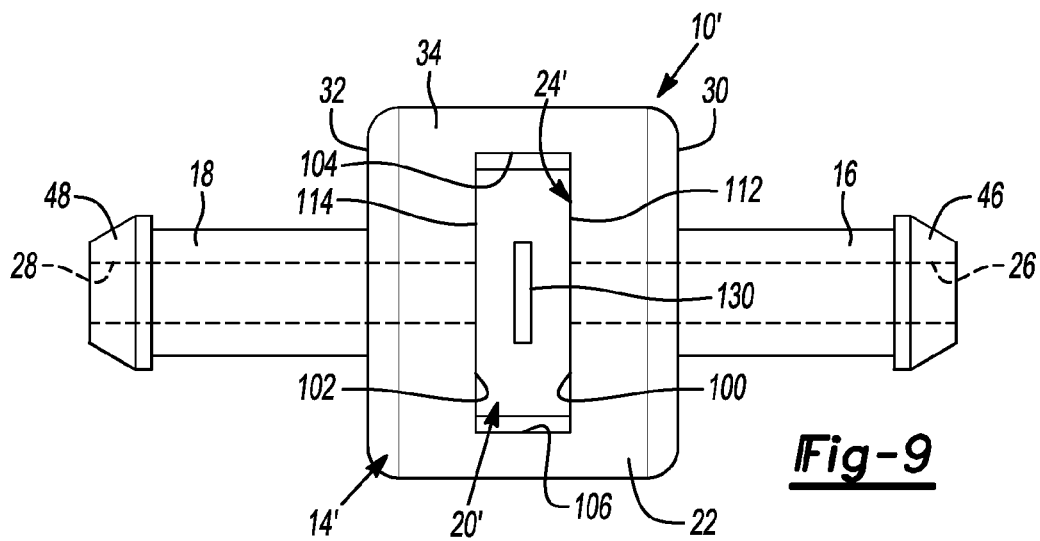
FIG. 9 is a side view of a second exemplary embodiment of the valve assembly shown in FIG. 1 and which is constructed in accordance with the present teachings.

With initial reference to FIG. 1 of the drawings, a vas valve assembly 10 according to the present teachings is shown to be implanted between a first end 12a of a vas deferens 12 and a second end 12b thereof. To accommodate implantation of valve assembly 10, vas deferens 12 can be surgically bifurcated, or a portion can be removed, to provide first end 12a and second end 12b thereof. As will be detailed, valve assembly 10 includes a housing 14 having an inlet section 16 adapted to be inserted into first end 12a of vas deferens 12 and an outlet section 18 adapted to be inserted into second end 12b of vas deferens 12. Pursuant to known surgical procedures, the ends 12a 12b can be attached to housing 14 via sutures and/or surgical adhesives to establish a definitive permanent implantation of valve assembly 10 with respect to vas deferens 12.

With reference to FIGS. 2 through 8, a first non-limiting embodiment of valve assembly 10 will now be described in detail. In general, valve assembly 10 can include housing 14 and a valve member 20. Housing 14 can include a central body section 22 defining a valve chamber 24 which is in fluid communication with an inlet passage 26 formed in tubular inlet section 16 and an outlet passage 28 formed in tubular outlet section 18. Body section 22 of housing 14 can have a cylindrical shape that is defined by a planar inlet face surface 30 from which inlet section 14 extends, a planar outlet face surface 32 from which outlet section 16 extends, and a circular peripheral surface 34 therebetween. As seen, valve chamber 24 extends radially inwardly from outer surface 34 and includes a first end 36, a second end 38, and a circular inner surface 40 so as to define a cylindrical valve chamber 24. Second end 38 of cylindrical valve chamber 24 can communicate with a retention chamber 42. Retention chamber 42 can be formed integrally in a closed end portion 44 of body section 22 (See FIG. 8) or, in the alternative, can be formed in a plug section 44' (shown in FIG. 3) that is rigidly installed within a throughbore version of valve chamber 24. Likewise, tubular inlet section 16 and outlet section 18 can be formed integrally with body section 22 or rigidly fixed thereto. It can be seen that frusto-conical flanged ends 46 and 48 are associated with the distal end of inlet and outlet sections 16 and 18, respectively, to assist in insertion and retention within vas deferens 12 so as to inhibit subsequent removeable therefrom.

Valve member 20 is installed within valve chamber 24 and defines an outer cylindrical surface 50 that is sized to have an outer diameter that is slightly smaller than the inner diameter of inner cylindrical surface 40 of valve chamber 24 so as to permit rotary movement of valve member 20 relative to housing 14. Valve member 20 can include a flow aperture 52 extending therethrough, a tool receipt feature 54 located adjacent open end 36 of valve chamber 24, and a valve retention feature 56 disposed within retention chamber 42. As best seen from FIGS. 2 through 4, flow aperture 52 is shown oriented to extend generally orthogonally with respect to a common flow axis defined by inlet passage 26 and outlet passage 28 when valve member 20 is located in a first or "closed" position. When located in its first position, valve member 20 interrupts and prohibits the flow of sperm from inlet passage 26 to outlet passage 28, whereby valve assembly 10 defines a "contraceptive" mode of functionality. Tool receipt feature 54 is shown as a slot 58 formed in a first end surface 60 of valve member 20 and extends parallel to flow aperture 52 so as to provide a visual indication to the surgeon that valve member 20 is located in its first position and valve assembly 10 is operating in its first mode. Specifically, when slot 58 is aligned transversely to tubular inlet section 16 and tubular outlet section 18 of housing 14 it provides a definitive visual indication that valve assembly 10 is closed.

Tool receipt feature 54 is also functional to permit the surgeon to rotate valve member 20 relative to housing 14 between the above-noted first position and a second or "open" position whereat flow aperture 52 is aligned with and permits sperm to flow therethrough between inlet passage 26 and outlet passage 28. With valve member 20 in its second position, valve assembly 10 defines a second or "reproductive" mode of functionality. With valve member 20 located in its second position, slot 58 extends parallel to tubular sections 16 and 18 of housing 14 to clearly provide a visual indication that valve assembly 10 is open.

As noted, valve member 20 can include valve retention feature 56 which has the dual function of retaining valve member 20 within valve chamber 24 of housing 14 and retaining valve member 20 in the selected one of its first and second positions. Specifically, valve retention feature 56 can include a pair of resilient first legs 66 and a pair of resilient second legs 68, both of which extend from a second end surface 70 of valve member 20. Upon installation of valve member 20 into housing 14, second end surface 70 of valve member 20 is seated on second end surface 38 within valve chamber 24. As best shown in FIG. 7, first legs 66 and second legs 68 are diametrically opposed and symmetrically oriented. In addition, first legs 66 are longer than second legs 68. Specifically, first legs 66 are sized to extend into and engage an inner wall surface of retention chamber 42.

The inner wall surface of retention chamber 42 can have a clover-leaf shape which defines a pair of first pockets 74 and a pair of second pockets 76. First pockets 74 and second pockets 76 are diametrically opposed and symmetrically oriented. As best seen in FIG. 8, each of first pockets 74 is disposed adjacent to a corresponding one of second pockets 76 but is separated therefrom by an inwardly projecting camming lobe 80. As such, the clover-leaf wall configuration defines a total of four pockets and four camming lobes. The drawings illustrate the pair of first legs 66 to be retained in the pair of first pockets 74 so as to locate and maintain valve member 20 in its first position. When it is desired to rotate valve member 20 to its second position, initial rotation of valve member 20 causes first legs 66 to resiliently inwardly deflect as they engage a pair of camming lobes 80. Upon about 90° of rotation, first legs 66 disengage camming lobes 80 and resiliently snap into engagement with second pockets 76 so as to locate and retain valve member 20 in its second position. It should be noted that valve member 20 can be rotated in either direction or through any range of angular motion. However, retention of first legs 66 within first pockets 74 definitively locates valve member 20 in its first position and retention of first legs 66 within second pockets 76 definitively locates valve member 20 in its second position. As noted, tool feature 54 provides the surgeon with a visual indication of whether valve member 20 is located in its first position or its second position.

Second legs 68 are shown resiliently deflected outwardly to have their flange surface 84 nested within an annular groove 86 formed in body section 22. Annular grove 86 can be located between valve chamber 24 and retention chamber 42. Thus, second legs 68 function to inhibit removal of valve member 20 from housing 14. FIG. 8 also illustrates a conical transition aperture 88 that is provided between valve chamber 24 and annular groove 86. Aperture 88 is configured to engage and inwardly deflect flange portions 84 of second legs 68 upon initial installation of valve member 20 into housing 14.

With reference now to FIGS. 9 through 12, a second non-limiting embodiment of a valve assembly 10' will now be described. Valve assembly 10' has many elements that are similar to valve assembly 10 such that similar elements are identified with common reference numerals. Valve assembly 10' also functions in a similar manner so as to establish a first or "contraceptive" mode when its valve member 20' is located in a first position and a second or "reproductive" mode when valve member 20' is located in a second position. With valve member 20' in its first position, flow aperture 52' is not aligned with inlet passage 26 and outlet passage 28 so as to prevent the flow of sperm therebetween. Conversely, when valve member 20' is located in its second position, flow aperture 52' permits fluid communication between inlet passage 26 and outlet passage 28. The primary distinction between valve assembly 10' and valve assembly 10 is that valve member 20' is slideably moveable between its first and second positions relative to housing 14' instead of being rotatably moveable.

Figures 10, 11:
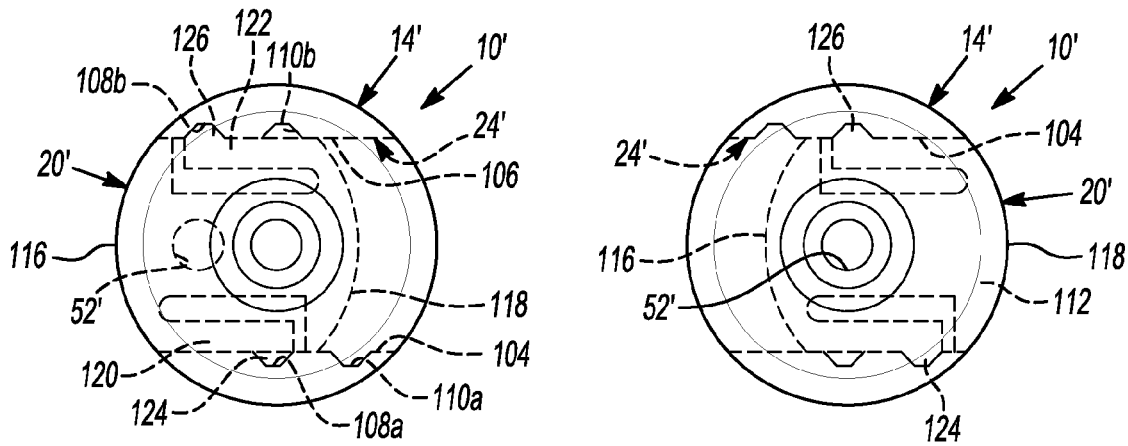
FIG. 10 is a sectional view through the valve assembly of FIG. 9.
FIG. 11 is another sectional that is similar to FIG. 10 with the exception that the valve member is located in a different position.
Figure 12:
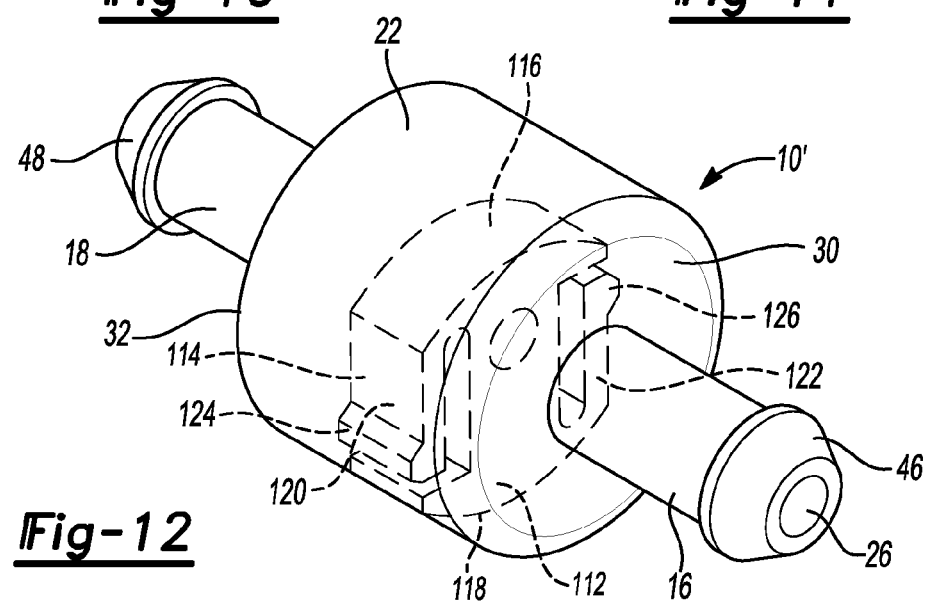
FIG. 12 is a perspective view of the valve assembly of FIGS. 9 through 11 with its housing shown in phantom.

As best seen from FIGS. 10 through 12, central body section 22 of housing 14' can include a valve chamber 24' which is in communication with inlet passage 26 and outlet passage 28. Valve chamber 24' is generally configured in a rectangular slot-like shape and is defined by an inlet face surface 100, an outlet face surface 102, a first edge surface 104, and a second edge surface 106. First edge surface 104 includes a first retention notch 108a and a second retention notch 110a. Similarly, second edge surface 106 includes a first retention notch 108b and a second retention notch 110b.

Valve member 20' is installed within valve chamber 24' and has a disc-shaped configuration including a planar front face surface 112 aligned in facing relationship with inlet face surface 100 of valve chamber 24' and a planar rear face surface 114 aligned in facing relationship with outlet face surface 102 of valve chamber 24'. Front face surface 112 and rear face surface 114 are bounded by a pair of arcuate edge surfaces 116 and 118. Valve member 20' further includes a valve retention feature that is disposed within valve chamber 24'. Specifically, the valve retention feature can include a first resilient leg 120 extending inwardly from edge surface 116 and a second resilient leg 122 extending inwardly from edge surface 118. First leg 120 has an end lug 124 that is adapted to slide against first edge surface 104 of chamber 24' and be retained in one of first notch 108a and second notch 110a. Likewise, second leg 122 has an end lug 126 that is adapted to slide against second edge surface 106 of chamber 24' and be retained in one of first notch 108b and second notch 110b.

From FIG. 10, valve assembly 10' is shown with valve member 20' located in its first or closed position such that fluid flow is interrupted between inlet passage 26 and outlet passage 28. Thus, valve assembly 10' is functioning in its first or contraceptive mode. With valve member 20' in its first position, lug 124 on first leg 120 is retained in first notch 108a while lug 126 on second leg 122 is retained in first notch 108b, thereby positively locating and retaining valve member 20' in its first position relative to housing 14'. In contrast, FIGS. 11 and 12 illustrate valve member 20' located in its second or open position such that fluid flow is permitted between inlet passage 26 and outlet passage 28 through flow aperture 52'. Thus, valve assembly 10' is functioning in its second or reproductive mode. With valve member 20' located in its second position, lug 124 on first leg 120 is retained in second notch 110a while lug 126 on second leg 122 is retained in second notch 110b. Legs 120 and 122 can be deflected inwardly to allow lugs 124 and 126 to slide along edge surfaces 104 and 106 when valve member 20' is moved between its first and second positions. A tool receipt feature in the form of a slot 130 can be provided in edge surface 116 of valve member 20' to permit the surgeon to engage and move valve member 20' between its two distinct positions. When slot 130 is aligned with outer surface 34 of body section 22, the surgeon has a visual indicator that valve member 20' is in its first position.

Likewise, when slot 130 is retracted relative to housing 14, the surgeon has a visual indication that valve member 20' is in its second position.

In accordance with the present disclosure, a method for use of valve assemblies 10 and 10' includes surgically implanting such dual mode contraceptive devices into the vas deferens 12 of a male patient. Upon initial implantation, the valve assembly can be shifted into either of its contraceptive or reproductive modes based on the desires of the patient. Upon the patient's subsequent decision to reverse the mode of functionality, the surgeon can perform a minor procedure to simply move the valve member to its other operative position. As such, the present invention permits selection between a pair of functional modes to meet the contraceptive or reproductive desires of the male patient. It is also contemplated that valve assemblies 10, 10' can be surgically implanted to reverse the effects of a previous vasectomy. Specifically, upon implantation, the valve assembly is place in its reproductive mode (i.e., valve open) to restore a fluid pathway between the free ends of the vas deferens. Accordingly, the present invention also provides a method for reversing a vasectomy without the need to undergo a vasovasostomy procedure.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A valve assembly for implantation into the vas deferens of a male patient, the valve assembly comprising:
    a housing including a body section defining a valve chamber, an inlet section having an inlet passage communicating with said valve chamber, and an outlet section having an outlet passage communicating with said valve chamber, wherein said inlet section is adapted to be inserted into a first free end of the vas deferens and said outlet section is adapted to be inserted into a second free end of the vas deferens;
    a valve member operably disposed within said valve chamber and having a flow aperture, a tool receipt feature, and a valve retention feature, said valve member is moveable within said valve chamber between first and second positions, said valve member is operable in its first position to inhibit fluid communication between said inlet passage and said outlet passage and is operable in its second position to permit fluid communication between said inlet passage and said outlet passage through said flow aperture, said tool receipt feature is operable to receive a tool for moving said valve member between its first and second positions, and said valve retention feature is operable to maintain said valve member in the selected one of its first and second positions while preventing removal of said valve member from said valve chamber;
    wherein said tool receipt feature is associated with a first end of said valve member and said valve retention feature is associated with a second end of said valve member; and
    wherein said valve retention feature includes a first leg disposed within a first retention pocket formed in a retention chamber when said valve member is located in its first position, wherein said first leg is disposed within a second retention pocket formed in said retention chamber when said valve member is located in its second position, and wherein a cam surface is disposed between said first and second pockets to assist in maintaining said first leg in a selected one of said first and second retention pockets.

2. The valve assembly of claim 1 wherein said retention chamber is formed in said body section of said housing and communicates with said valve chamber.

3. The valve assembly of claim 2 wherein said valve retention feature further includes a second leg biased into retention within an annular groove formed in said body section of said housing.

4. The valve assembly of claim 3 wherein said annular groove is disposed between said valve chamber and said retention chamber.

5. The valve assembly of claim 1 wherein said valve member is rotatably supported within said valve chamber for rotary movement between its first and second positions.

6. The valve assembly of claim 1 wherein said valve member is slidably supported within said valve chamber for translational movement between its first and second positions.

7. A valve assembly for implantation into the vas deferens of a male patient, the valve assembly comprising:
    a housing including a body section defining a valve chamber and a retention chamber, an inlet section having an inlet passage communicating with said valve chamber, and an outlet section having an outlet passage communicating with said valve chamber, wherein said inlet section is adapted to be inserted into a first end of the vas deferens and said outlet section is adapted to be inserted into a second end of the vas deferens; and
    a valve member rotatably supported in said valve chamber for rotation between first and second positions, said valve member having a flow aperture, a tool receipt feature and a valve retention feature, said valve member is operable in its first position to orient said flow aperture to inhibit fluid communication between said inlet passage and said outlet passage and is operable in its second position to orient said flow aperture to permit fluid communication between said inlet passage and said outlet passage, said tool receipt feature is associated with a first end portion of said valve member and is adapted to receive a tool to facilitate rotation of said valve member between its first and second positions, and said valve retention feature is associated with a second end portion of said valve member and includes a leg member extending into said retention chamber for maintaining said valve member in the selected one of its first and second positions; and
    wherein said retention chamber includes a first retention pocket and a second retention pocket, and wherein said leg is disposed within said first retention pocket when said valve member is rotated to its first position and said leg is disposed within said second retention pocket when said valve member is rotated to its second position.

8. The valve assembly of claim 7 wherein said retention chamber communicates with said valve chamber.

9. The valve assembly of claim 8 wherein said valve retention feature further includes a second leg biased into retention within an annular groove formed in said body section of said housing.

10. The valve assembly of claim 9 wherein said annular groove is disposed between said valve chamber and said retention chamber.

11. A valve assembly for implantation into the vas deferens of a male patient, the valve assembly comprising:
a housing including a body section defining a valve chamber, an inlet section having an inlet passage communicating with said valve chamber, and an outlet section having an outlet passage communicating with said valve chamber, wherein said inlet section is adapted for insertion into a first end of the vas deferens and said outlet section is adapted for insertion into a second end of the vas deferens; and
a valve member supported for sliding movement within said valve chamber between first and second positions, said valve member having a flow aperture, a tool receipt feature and a valve retention feature, said valve member is operable in its first position to orient said flow aperture so as to inhibit fluid communication between said inlet passage and said outlet passage and is operable in its second position to orient said flow aperture to permit fluid communication between said inlet passage and said outlet passage, said tool receipt feature is associated with one end of said valve member to facilitate translational movement of said valve member between its first and second positions, and said valve retention feature includes a first leg formed along a first lateral edge of said valve member, a second leg formed along a second lateral edge of said valve member, a pair of first retention notches formed in edge surfaces of said valve chamber that are adapted to retain said first and second legs therein when said valve member is located in its first position, and a pair of second retention notches formed in said edge surfaces of said valve chamber that are adapted to retain said first and second legs therein when said valve member is located in its second position.

* * * * *